(12) United States Patent
Phelan et al.

(10) Patent No.: US 8,691,198 B2
(45) Date of Patent: Apr. 8, 2014

(54) ENVIRONMENTALLY BENIGN PLASTICIZERS BASED ON DERIVATIVES OF ACETONE

(75) Inventors: Gregory David Phelan, Cortland, NY (US); William Brenden Carlson, Seattle, WA (US)

(73) Assignee: Somogyi AgTech LLC, Holualoa, HI (US)

( * ) Notice: Subject to any disclaimer, the term of this patent is extended or adjusted under 35 U.S.C. 154(b) by 0 days.

(21) Appl. No.: 13/170,055

(22) Filed: Jun. 27, 2011

(65) Prior Publication Data

US 2011/0318292 A1 Dec. 29, 2011

Related U.S. Application Data

(60) Provisional application No. 61/358,769, filed on Jun. 25, 2010.

(51) Int. Cl.
*A61K 8/30* (2006.01)
*A61K 8/49* (2006.01)

(52) U.S. Cl.
USPC .......................... 424/70.1; 424/59

(58) Field of Classification Search
None
See application file for complete search history.

(56) References Cited

U.S. PATENT DOCUMENTS

| | | | |
|---|---|---|---|
| 3,010,973 A | 11/1961 | Hirsch | |
| 3,169,879 A | 2/1965 | Wahl | |
| 5,458,872 A * | 10/1995 | Durand | 424/59 |
| 5,679,656 A * | 10/1997 | Hansenne | 514/54 |
| 5,693,670 A * | 12/1997 | Philippe et al. | 514/545 |
| 5,955,034 A | 9/1999 | Zaunbrecher | |
| 5,972,313 A * | 10/1999 | Tuloup et al. | 424/59 |
| 7,659,420 B2 * | 2/2010 | Putnam et al. | 558/264 |
| 7,879,958 B2 * | 2/2011 | Luo et al. | 526/84 |
| 2002/0128153 A1 * | 9/2002 | Narayanan et al. | 504/232 |
| 2003/0162671 A1 * | 8/2003 | Kalota et al. | 508/154 |
| 2003/0185769 A1 * | 10/2003 | Ehlis et al. | 424/59 |
| 2006/0045856 A1 * | 3/2006 | Mujica et al. | 424/59 |
| 2007/0191256 A1 * | 8/2007 | Fossum et al. | 510/515 |
| 2008/0194786 A1 * | 8/2008 | Putnam et al. | 528/44 |
| 2009/0043055 A1 * | 2/2009 | Luo et al. | 526/66 |

FOREIGN PATENT DOCUMENTS

| | | |
|---|---|---|
| EP | 2258430 A2 * | 12/2010 |
| WO | 2005/108457 A1 | 11/2005 |

OTHER PUBLICATIONS

Garson et al. Monomer and dimer formation in esters of dihydroxyacetone. Can. J. Chem. v47, 1969:1249.*
Jung, S.-H., et al., "An Efficient Multigram-Scale Preparation of Dihydroxyacetone Phosphate," Journal of Organic Chemistry 59(23):7182-7184, Nov. 1994.
Yuasa, H., et al., "Studies on the Unusual Stability of cis-2,5-Diethoxy-2,5-bis(hydroxymethyl)-1,4-dioxane," Tetrahedron 55(8):2193-2204, Feb. 1999.
Zelikin, A.N., and D. Putnam, "Poly(carbonate—acetal)s From the Dimer Form of Dihydroxyacetone," Macromolecules 38(13):5532-5537, Jun. 2005.
International Search Report and Written Opinion, mailed Feb. 9, 2012, issued in corresponding International Application No. PCT/US2011/042057, filed Jun. 27, 2011, 12 pages.
Zelikin, A.N., et al., "A Functionalizable Biomaterial Based on Dihydroxyacetone, an Intermediate of Glucose Metabolism," Biomacromolecules 7(11):3239-3244, Nov. 2006.

* cited by examiner

*Primary Examiner* — Robert A Wax
*Assistant Examiner* — Olga V Tcherkasskaya
(74) *Attorney, Agent, or Firm* — Christensen O'Connor Johnson Kindness PLLC

(57) ABSTRACT

Compounds derived from acetone are provided. Particularly, the compounds are derivatives of hydroxyacetone, including dimers of both 1-hydroxyacetone and 1,3-dihydroxyacetone. The hydroxy moieties on the core hydroxyacetone molecule serves as an attachment point for a variety of moieties (e.g., ethers, esters, phosphorous containing, or nitrogen containing) that are selected to provide the compound with a particular property. Applications of the compounds include plasticizers, supersurfactants, and additives for health care products, such as shampoo and perfume.

19 Claims, 16 Drawing Sheets

Plasticizer, Bis-isovalerate ester of
2,5-Diethoxy-1,3-dihydroxyacetone dimer

Plasticizer, Bis-phosphinate ester of
2,5-Diisopropoxy-1,3-dihydroxyacetone dimer Plasticizer based upon glucolaldehyde dimer
R = carboxylic acid, fatty acid, phosphate, silicone, ethyl, ester, alkyl, carbocyclic

ENVIRONMENTALLY BENIGN PLASTICIZERS BASED ON DERIVATIVES OF ACETONE

CROSS-REFERENCE TO RELATED APPLICATION

This application claims the benefit of U.S. Provisional Application No. 61/358769, filed Jun. 25, 2010, the disclosure of which is incorporated herein by reference in its entirety

BACKGROUND

Plasticizers are additives to plastics that increase flexibility and durability of hard, rigid plastics. In many ways they are like high boiling solvents for plastics that do not evaporate. The global usage of phthalate plasticizers is 11 billion pounds per year at a value exceeding $30 billion. Phthalate plasticizers have come under great scrutiny recently due to their toxicity and persistence in the environment. For instance, the plasticizer bis-2-ethylhexyl phthalate poses a risk to human development and fertility and has been found to be a carcinogen and a toxin to reproductive systems. Thus, there is a need for new plasticizers that do not pose these problems and are environmentally benign.

Acetone is one of the most widely produced and used chemicals. It is used extensively in the plastics industry. Sixty-six percent of acetone is used to make methyl methacrylate and bisphenol-A. Seventeen percent of acetone is used as a zero VOC solvent for coatings. The remainder is used to produce other chemicals such as methyl isobutyl ketone and cyanohydrins. The plasticizer industry would pose a significant gain for acetone producers if acetone could be used as a feedstock to manufacture plasticizers that would replace or augment the present use of phthalate plasticizers.

SUMMARY

This summary is provided to introduce a selection of concepts in a simplified form that are further described below in the Detailed Description. This summary is not intended to identify key features of the claimed subject matter nor is it intended to be used as an aid in determining the scope of the claimed subject matter.

Compounds derived from acetone are provided. Particularly, the compounds are derivatives of hydroxyacetone, including dimers of both 1-hydroxyacetone and 1,3-dihydroxyacetone. The hydroxy moieties on the core hydroxyacetone molecule serves as an attachment point for a variety of moieties (e.g., ethers, esters, phosphorous containing, or nitrogen containing) that are selected to provide the compound with a particular property. Applications of the compounds include plasticizers, supersurfactants, and additives for health care products, such as shampoo and perfume.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Aspects of the invention include a series of molecules of various structural forms that are useful in embodiments as plasticizers and additives to plastic/polymer materials or as additives for personal care products such as perfume and shampoo. Compositions and products that include the molecules are also disclosed. The molecules are generally manufacturable from acetone, one of the most widely produced chemicals in the world. The invented plasticizers are primarily esters of a cyclic form of acetone that is in the family of carbohydrates and as such have very low toxicity. The result is an environmentally benign, biodegradable family of plasticizers that do not encompass the detrimental features (carcinogenic, reproductive, and developmental toxins) of phthalate plasticizers. Being a derivative of acetone, the plasticizers furthermore constitute a cost effective approach to the elimination of the problems associated with phthalate plasticizers.

Figure 1:
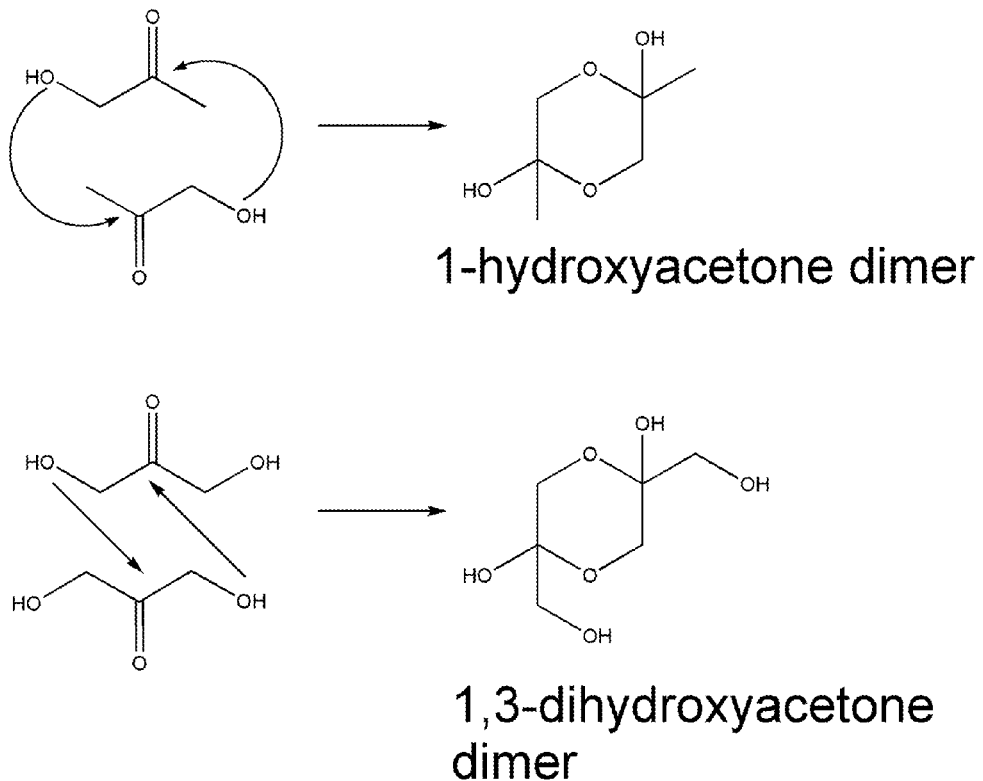
FIG. 1. Acetone derivatives 1-Hydroxyacetone (acetol) and 1,3-dihydroxyacetone and their dimers in accordance with the embodiments provided herein.

Acetone is one of the top produced industrial chemicals in terms of tonnage. U.S. production capacity for acetone reached 1,839 thousand metric tons (4,055 million pounds) in 2002. Demand for acetone in the U.S. alone was 1,189 thousand metric tons (2,621 million pounds). Forty-two percent of the acetone produced is used in the manufacture of methyl methacrylate and twenty-four percent is used in the manufacture of bisphenol-A. Acetone is extensively used as a solvent as it does not harm the atmosphere and as such is a zero VOC (volatile organic content) solvent that can be engaged without penalty. Acetone is extremely low in toxicity and is a natural product of the human body's metabolism. The invention utilizes derivatives of acetone called 1-hydroxyacetone (acetol) and 1,3-dihydroxyacetone. 1-Hydroxyacetone (acetol) and 1,3-dihydroxyacetone can be dimerized to form high boiling cyclic compounds (FIG. 1). Plasticizers can be produced from 1-hydroxyacetone, 1,3-dihydroxyacetone, or their dimers.

1,3-Dihydroxyacetone is widely used in the food and fragrances industry. The compound is used in everything from candy to spices to impart flavor, sweetness, and smell. 1,3-Dihydroxyacetone is used at a concentration of 1200 ppm in hard candy and up to 2400 ppm in various spices. The $LD_{50}$ (oral, rat) for 1,3-dihydroxyacetone dimer is in excess of sixty thousand mg/kg. Thus the acute toxicity of 1,3-dihydroxyacetone and its dimer is extremely low. The acetone derivatives are not known to act as carcinogens, mutagens, reproductive or developmental toxins. In fact 1,3-hydroxyacetone and its dimer are the most simple from of ketose and as such belong to the carbohydrate family. The inventors believe that the use of these acetone derivatives as plasticizers in polymers and coatings has never been disclosed. However, the high boiling point (480° C.) and other physical properties of the compounds, along with the low toxicity, non-carcinogenicity, and cost effectiveness, compounds are an attractive alternative to the existing toxic phthalate plasticizers.

However, there are particular properties that a plasticizer must have to increase the flexibility and durability of plastics. These properties are:

The enthalpy of mixing ($\Delta H$) of the plasticizer into the polymer is exothermic for increased stability;

The Gibbs free energy ($\Delta G$) of mixing the plasticizer into the polymer is spontaneous;

The plasticizer should have a high solubility in the plastic being plasticized;

The plasticizer should have very low vapor pressure to prevent evaporation out of the polymer;

The plasticizer should have very low solubility in any solvent that the end product be exposed to prevent leeching of the plasticizer; and The plasticizer should be sufficiently large to spread the polymer chains apart to increase the free volume of the plastic.

The provided plasticizers meet these criteria.

Polymers of like structure are usually not soluble in each other; for example, polyethylene and polypropylene are not soluble in each other and phase separate. The reason for phase separation is that the enthalpy of mixing is small as there is very little thermodynamic interaction between the chains. For this reason polymer alloys are rare.

Figure 2:
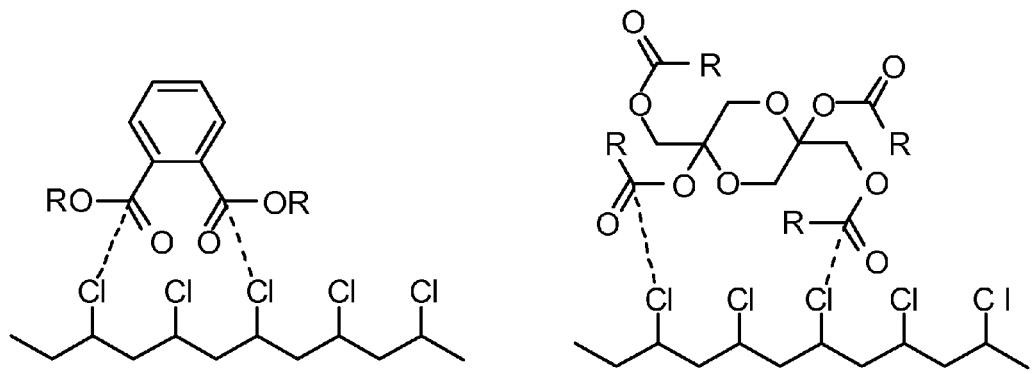
FIG. 2. Diagram of the thermodynamic interaction between phthalate-PVC and acetone-PVC plasticizers in accordance with the embodiments provided herein. The carbonyl of the plasticizer and the PVC chloride interact with each other.

There needs to be enthalpy of mixing for the plasticizer/polymer combination for the system to be stable and not phase separate. In the case of polymers such as polyvinyl chloride, which is a common polymer that is combined with a plasticizer, the provided plasticizers are completely compatible because the ester linkage-chloride interaction leads to an exothermic heat of mixing and therefore to a stable combination (FIG. 2). In FIG. 2, the thermodynamic interactions between phthalate and PVC, and acetone-derived plasticizer and PVC, are diagrammatically illustrated. The carbonyl of the plasticizer and the PVC chloride interact with each other. The acetone derivatives can be formulated to have more ester moieties per compound so as to increase thermodynamic interaction and improve plasticizer ability.

The acetone dimer plasticizers also have sufficient size to allow for free motion of the polymer chains and for a sufficiently high boiling point as to minimize evaporation. Lastly, there can be up to four ester moieties on the acetone dimer plasticizers which greatly increase the thermodynamic interaction between polymer host and plasticizer. The increased interaction decreases the chance of the plasticizer being leached out.

A variety of structural forms of the 1,3-dihydroxyacetone dimer can be made into useful materials utilized as additives for plastic materials and personal care products. The hydroxyl moieties of the 1,3-dihydroxyacetone dimer can be made into non-limiting examples including esters, ethers, and urethanes. The 2,5 hydroxy methyl moieties of the 1,3-dihydroxyacetone dimer can be oxidized to carboxylic acid moieties. These carboxylic moieties can produce structural forms of the 1,3-dihydroxyacetone dimer that non-limiting examples include esters, amides, thio-esters, phosphorous containing esters, ethers, and the like. Any of these structural forms of the invention can be utilized as additives to plastics, plasticizers, additives to personal care products.

In one aspect, a plasticizer is provided, comprising a compound:

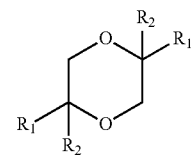

wherein $R_1$ is independently selected from —O—$R_3$ and —$CH_2$—O—$R_3$;

wherein $R_2$ is independently selected from H, —O—$R_3$, C—O—C(O)—$R_3$, C—O—X(O)$_{1\,or\,2\,or\,3}$—$R_3$ where X is C, Si, Ge, Sn, Pb, P, As, Sb, Bi, S, Se, Te; methyl, lower alkane, ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety; and wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

In another aspect, a plasticizer is provided, comprising a compound selected from the group consisting of a 1-hydroxyacetone dimer and a 1,3-dihydroxyacetone dimer.

In another aspect, a plasticizer is provided, comprising a compound selected from the group consisting of a carboxylic acid derived from 1-hydroxyacetone dimer and a 1,3-dihydroxyacetone dimer.

In another aspect, a compound is provided:

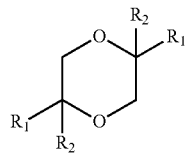

wherein $R_1$ is independently selected from the group consisting of $-O-R_3$, $-CH_2-O-R_3$,

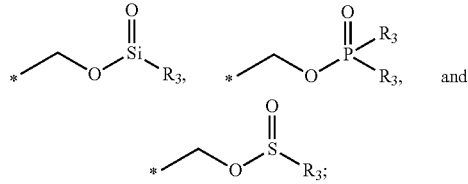

wherein $R_2$ is independently selected from H, $C-O-C(O)-R_3$, $C-O-X(O)_{1\,or\,2\,or\,3}-R_3$ where X is C, Si, Ge, Sn, Pb, P, As, Sb, Bi, S, Se, Te; methyl, lower alkane, ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety; and wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

In another aspect, a compound is provided:

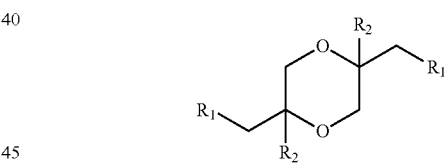

wherein $R_1$ and $R_2$ are independently selected from the group consisting of:

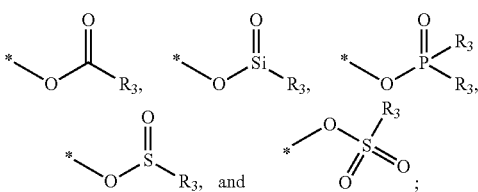

wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

In another aspect, a compound is provided:

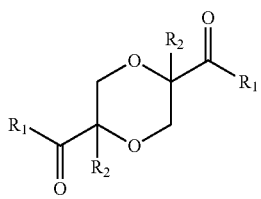

wherein $R_1$ and $R_2$ are independently selected from the group consisting of:

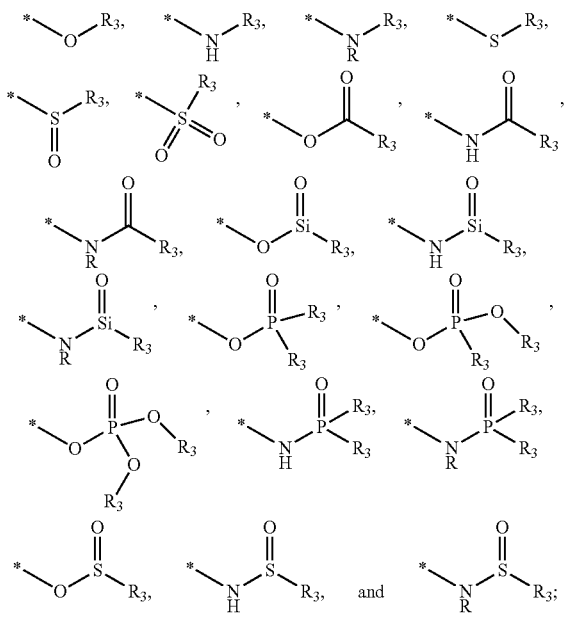

wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

In another aspect, a plasticizer is provided, comprising a compound:

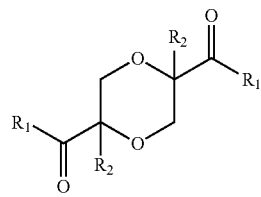

wherein $R_1$ and $R_2$ are independently selected from the group consisting of:

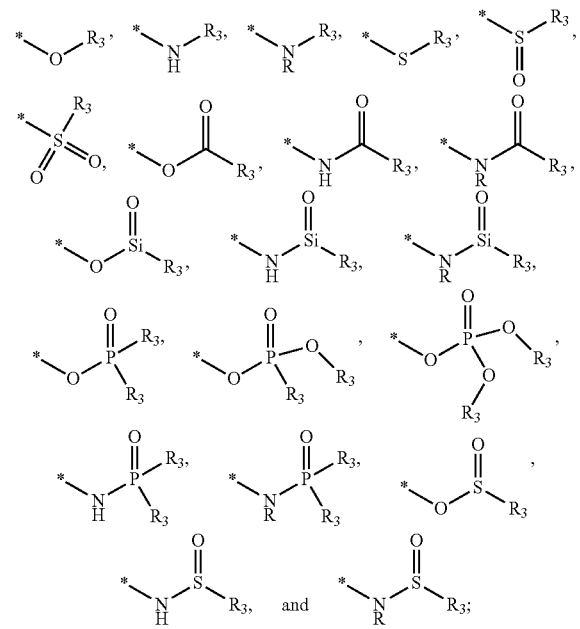

wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

In another aspect, a plasticizer is provided, comprising a compound:

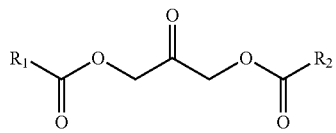

wherein $R_1$ and $R_2$ are independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

In certain embodiments, the provided compounds are formed by the reaction of a hydroxyacetone dimer and a carboxylic acid.

In certain embodiments, $R_3$ is a naturally occurring acid. Such acids include: animal fatty acids, animal acids, vegetation fatty acids, vegetation acids, bacteria derived acids, single cell organism derived acids, virus derived acids, and fruit-derived acids.

In certain embodiments, the plasticizer or compound is selected from the group consisting of biodegradable, biocompatible, low in toxicity, non-carcinogenic, not harmful to the reproductive tract, non-mutagenic, non-teratogenic, and low in health consequences.

In certain embodiments, the provided compound has a boiling point of 100° C. or greater. In certain embodiments, the provided compound has a freezing point of 20° C. or less.

In certain embodiments, the provided compound is a liquid or a solid.

In certain embodiments, the provided compound is colorless.

In certain embodiments, the provided compound has color.

In certain embodiments, the provided compound is tasteless.

In certain embodiments, the provided compound has taste.

In certain embodiments, the provided compound is incorporated into a polymer matrix.

In certain embodiments, the provided compound is a dimer of a glucolaldehyde, or derivative thereof.

In certain embodiments a composite is provided, comprising:
(a) concrete; and
(b) a compound as provided herein incorporated into the concrete.

In certain embodiments a composite is provided, comprising:
(a) a polymer; and
(b) a compound as provided herein incorporated into the polymer. An exemplary polymer is PVC. The polymer is a polymer that a user requires to be softened for a particular application. Accordingly, the provided compounds can be integrated into the polymer matrix as a plasticizer to soften the polymer matrix. This allows for easier processing and less rigid and brittle polymer material to form into a product.

Articles may also be formed that incorporate the provided compounds. Exemplary articles include a wire, tubing, tile, paint, a bottle, a panel, a communication device, a computing device, a wind, a vehicle, a structural unit, cloth, fabric, carpet, and a foam.

Synthesis of the Plasticizers

In representative embodiments, the invention is made by the formation of an ester, ether, urethane linkage, silane, or thioester between dihydroxyacetone, hydroxyacetone or their dimers and an organic species.

Standard chemical synthetic techniques known to those of skill in the art are used to synthesize the plasticizers.

A typical synthesis begins with hydroxyacetone. If a monohydroxyacetone is used, the hydroxy group is reacted to form the desired ether, ester, etc. "arms" extending from the site of the hydroxy group. Similarly, if a dihydroxyacetone is used, either two identical arms are formed at each hydroxy site, or one site can be protected while the other is reacted with a first moiety to provide a first arm, the second hydroxy site is then deprotected or otherwise manipulated to attach a moiety to form a second arm. If the hydroxyacetone is dimerized, as in FIGS. 1 and 4, additional hydroxy sites are available for attachment of arm moieties.

There are a variety of ways to make 1,3-dihydroxyacetone. Using acetone, the acetone is reacted with chlorine to produce 1,3-dichloroacetone, which is then hydrolyzed to 1,3-dihydroxyacetone. 1,3-dihydoxyacetone is also naturally produced in biological processes. Using selective oxidation of glycerol using either or both enzymatic or inorganic catalysts can produce 1,3-dihydroxyacetone. Using catalysts and polymer supports, 1,3-dihydroxyacetone can be produced from formaldehyde. Once 1,3-dihydroxyacetone is produced, it naturally cyclizes, much in the same way the glucose naturally forms the pyranose structure.

The "arm" moieties that attach to the hydroxyacetone at a hydroxy site can be any functionality known to form a bond with a hydroxy moiety. These arms are typically functionalized with a chloride or acid (e.g., a carboxylic acid).

Figure 4:
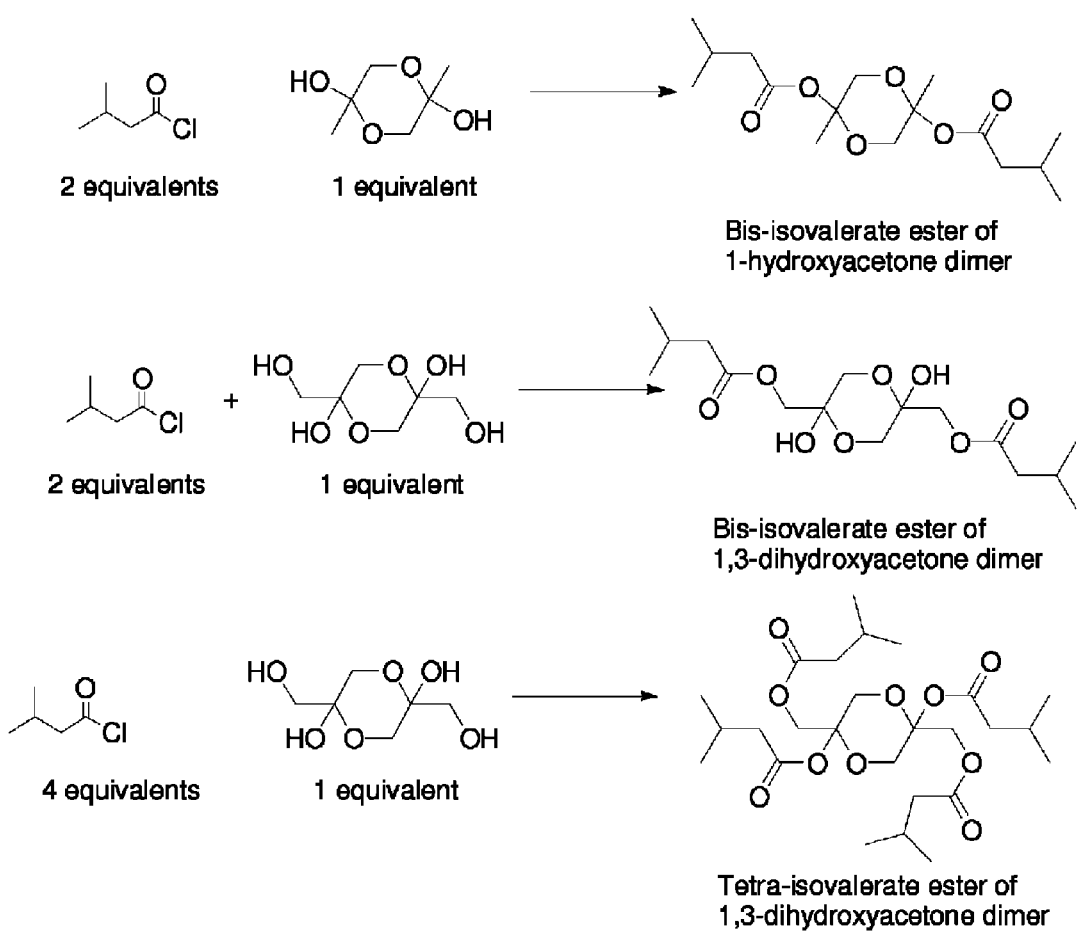
FIG. 4. Reaction sequences to form the bis-isovalerate ester of 1-hydroxyacetone dimer and 1,3-dihydroxyacetone dimer from the acetone dimers and isovaleric anhydride, and the tetra-isovalerate ester from 1,3-dihydroxyacetone dimer in accordance with the embodiments provided herein.

A number of representative synthetic schemes are illustrated in FIG. 4, which illustrates reaction sequences to form the bis-isovalerate ester of 1-hydroxyacetone dimer and 1,3-dihydroxyacetone dimer from the acetone dimers and isovaleric anhydride, and the tetra-isovalerate ester from 1,3-dihydroxyacetone dimer. This structure type of plasticizer with relatively small ester moieties would be the most common type of plasticizer employed.

If an acid is used to coordinate an arm to the hydroxyacetone, the acid is selected from a carboxylic acid, fatty acid, phosphoric acid ester, phosphinic acid, thiocarboxylic acid, silicone, silane, or urethane with an isocyanate. Thus there is a choice of acid to use to produce the plasticizer. It is logical to use naturally occurring carboxylic acids or derivatives of carboxylic acids to create an environmentally benign plasticizer. Aromatic acids such as benzoic acid would not be a preferred acid to create an environmentally benign plasticizer. Thus, acids from natural sources such as plants are ideal. Fruits such as bananas, apples, or pears and saponification of fats and triglycerides are prime sources for naturally occurring organic carboxylic acids.

Table 1 lists several naturally occurring carboxylic acids, their toxicity data, and where they occur naturally. There are other sources of these acids other than agriculture; for instance isovaleric acid can be obtained as the triglyceride from animal fats. Usually the carboxylic acid is in the form of an ester. Isovaleric acid is found in apples as the ester ethyl isovalerate. Esters with 1-hydroxyacetone and 1,3-dihydroxyacetone and their dimers can be formed with any of the acids shown, but isovaleric acid will be used as an example since it is very low in toxicity, benign to the environment, and is inexpensive.

mental and toxicity advantages over naphthalene based supersurfactants and have a cost advantage over polycarboxylate ethers. Supersurfactants are often employed in concrete as a way to limit the amount of water used. The strength of concrete is an inverse function of water; thus, limiting the amount of water used makes for stronger concrete. However, limiting the amount of water leads to the slurry being very

TABLE 1

Various carboxylic acids, their structure, and sources.

| Acid | Structure | $LD_{50}$(rat) mg/kg | Source | Acid | Structure | $LD_{50}$(rat) × mg/kg | Source |
| --- | --- | --- | --- | --- | --- | --- | --- |
| Acetic Acid | 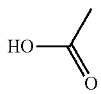 | 3310 | Geranium, Lavendar, Sage, Pineapple, Strawberry, Oxidation of ethanol | Caprylic acid | 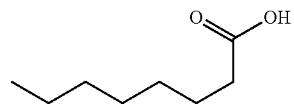 | 600 | Oranges, Goat Milk, coconuts |
| Isovaleric acid | 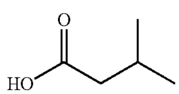 | 3200 | Apples | Heptanoic Acid | 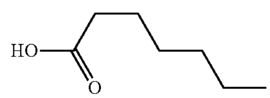 | 7000 | apricot, cherry, grape, raspberry |
| Butyric acid | 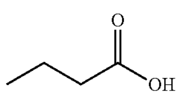 | 2940 | Pineapple, cherry, peach, apple, strawberry | Caproic acid | 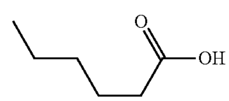 | 3000 | pineapple, banana, apple |
| Pentanoic Acid | 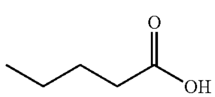 | 1844 | Apple | | | | |

Figure 3:
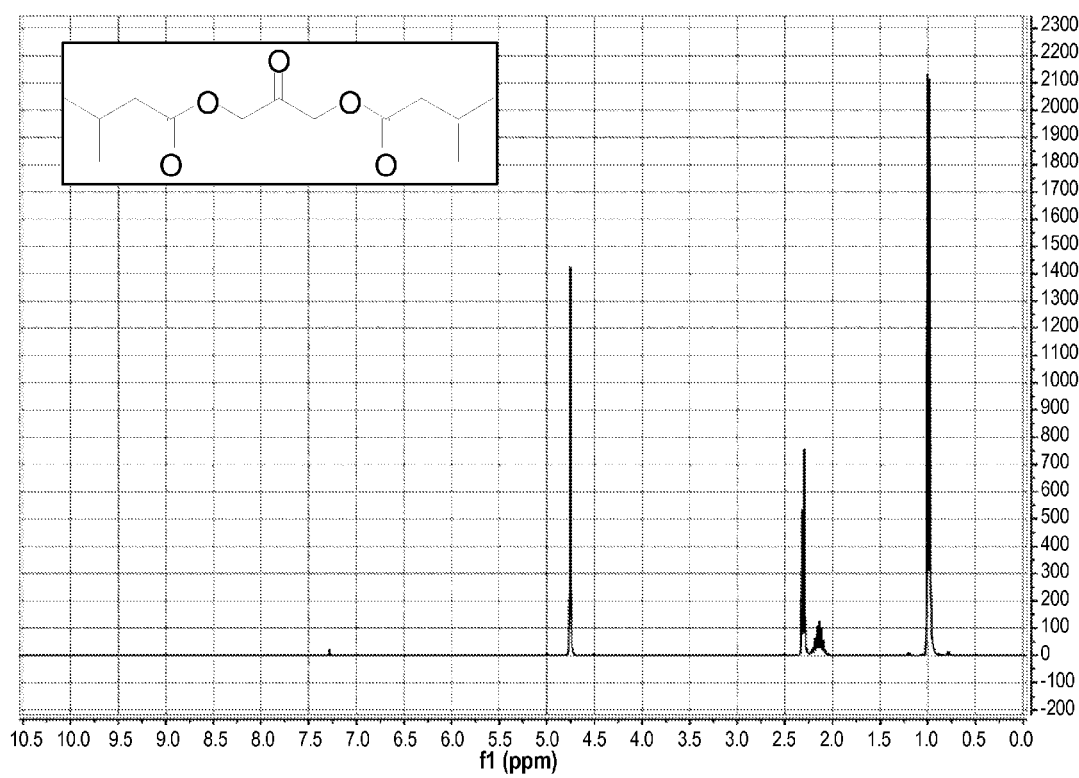
FIG. 3. $^1$H NMR in $DCCl_3$ of bis-isovalerate ester of 1,3-dihyroxyacetone in accordance with the embodiments provided herein.

Synthesis of isovalerate esters of 1-hydroxyacetone and 1,3-dihydroxyacetone and their dimers. Two and a half equivalents of isovaleric chloride was added to an anhydrous solution of triethylamine in methylene chloride at −20° C. To the solution was added anhydrous 1-hydroxyacetone, 1,3-dihydroxyacetone, or the dimer of 1-hydroxyacetone, or the dimer of 1,3-dihydroxyacetone. The acetone derivatives are allowed to dissolve into the isovaleric chloride solution. The solution was allowed to warm to room temperature overnight to form the mono-isovalerate ester of 1-hydroxyacetone or the bis-isovalerate ester of 1,3-dihydroxyacetone or the dimers. Four equivalents of isovaleric chloride were used to one equivalent of anhydrous 1,3-dihydroxyacetone dimer to create the tetra-ester. The compounds were purified by first washing with a dilute bicarbonate solution and then chromatographed on a silica column using 2% acetone in hexanes. Yields were close to quantitative. NMR of 1,3-dihydroxyacetone di-isovalerate ester is shown in FIG. 3.

Ether-Ester combination. Ethers may also be used in the formation of plasticizers from hydroxyacetone. The ether moiety is used to cap the hydroxy moieties while the esters cap the methyl alcohol moieties. Ethers are typically more hydrolytically stable and hydrolyze only under very acidic conditions. Alcohols such as ethanol or isopropanol can be reacted with 1-hydroxyacetone or 1,3-dihydroxyacetone or their dimers to form plasticizers suitable for organic coatings based upon acrylics, styrenics, vinyl acetate and many more.

Using PEG, sulfonates, and other water soluble or water solubilizing moieties a series of supersurfactants can be formed. Supersurfactants based upon dimers of 1-hydroxyacetone dimer or 1,3-dihydroxyacetone have several environdifficult to flow and work with. Supersurfactants allow for better flow properties and make the concrete easier to work with when water is limited.

Accordingly, in certain aspects and embodiments, the plasticizers are used as supersurfactants in concrete (e.g., as an additive to concrete to enhance strength).

Figure 5:
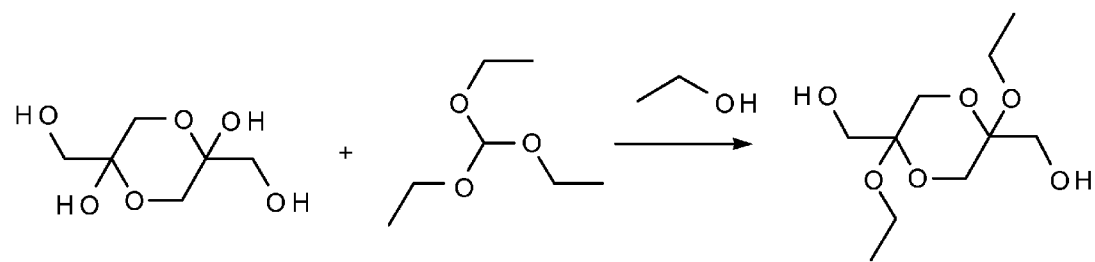
FIG. 5. Synthesis scheme for 2,5-diethoxy-1,3-dihydroxyacetone dimer in accordance with the embodiments provided herein.
Figure 6:
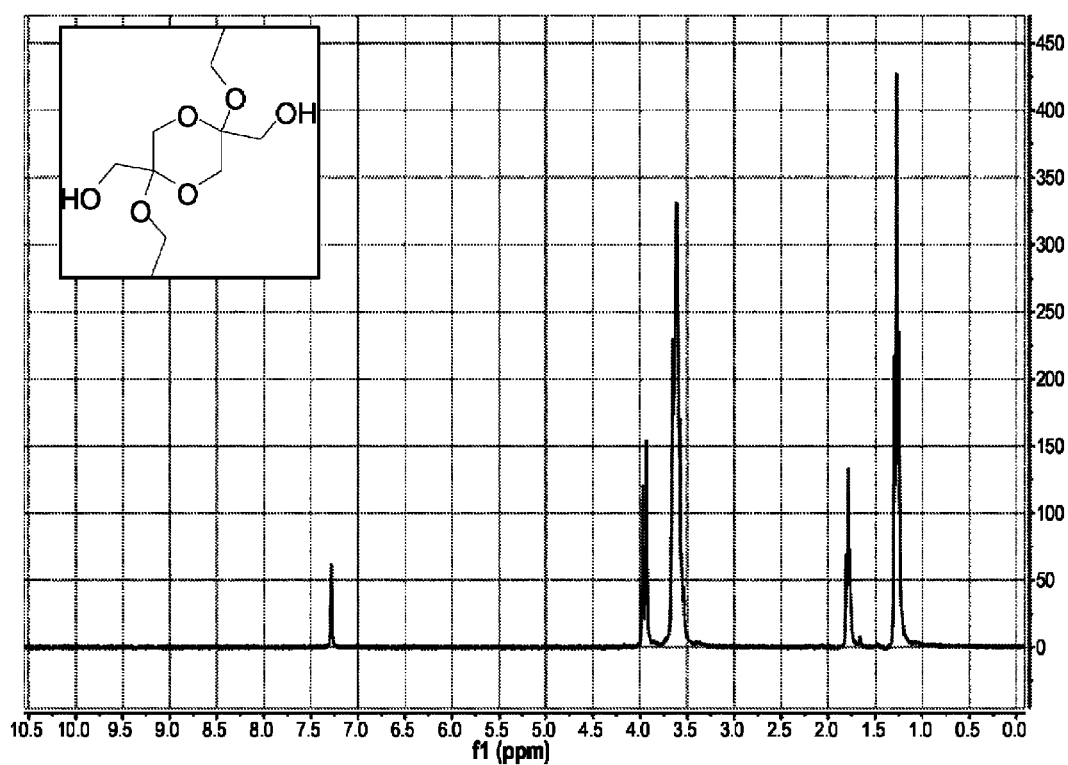
FIG. 6. $^1$H NMR in $DCCl_3$ of 2,5-diethoxy-1,3-dihydroxyacetone dimer in accordance with the embodiments provided herein.
Figure 7:
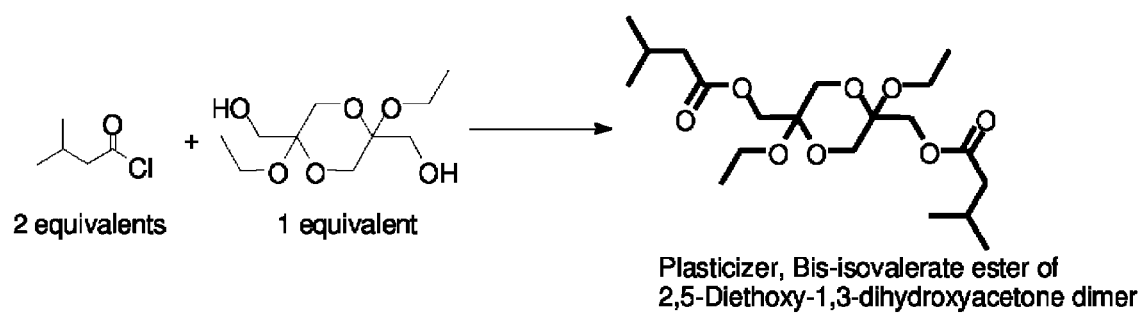
FIG. 7. Scheme to result in a plasticizer of bis-isovalerate ester of 2,5-diisopropoxy-1,3-dihydroxyacetone dimer in accordance with the embodiments provided herein. The ethyl moieties can be changed to methyl, isopropyl or other organic.

Synthesis of (2,5-Diisopropoxy-1,3-dihydroxyacetone dimer bis isovalerate ester, FIGS. 5-7). Dihydroxyacetone dimer (32 g) and p-toluenesulfonic acid (130 mg) were combined in a two-heck flask and placed under dry nitrogen. Triethyl orthoformate, 60 mL, was combined with 300 mL of 200 proof anhydrous ethanol and together they were added to the dihydroxyacetone dimer and p-toluenesulfonic acid. The mixture was stirred for 24 h, after which time 400 mg of $Na_2CO_3$ was added, and the reaction mixture stirred for an additional 30 min and filtered. Removal of the solvent and residual triethyl orthoformate in vacuo and recrystallization of the product from ethyl acetate resulted in 2,5-diethoxy-1,3-dihydroxyacetone dimer in 75% yield (FIG. 5). $^1$H NMR in FIG. 6. Substitution of triisopropyl orthoformate and isopropanol for ethanol results in the isopropyl ether in 90% yield. $^1$H NMR (CDCl3) δ. 1.18-1.26 (12H); 3.4-4.2(10H).

To form the bis isovalerate ester, 2,5-Diethoxy-1,3-dihydroxyacetone dimer (one equivalent) was dissolved in anhydrous mixture of triethylamine in methylene chloride and cooled to 0° C. Two and a half equivalents of isovaleric chloride was added to the 2,5-diethoxy-1,3-dihydroxyacetone solution using an addition funnel with dropwise addition. The solution was mixed vigorously during the addition. The solution was allowed to slowly warm to room temperature overnight to form the bis-isovalerate ester of 2,5-diethoxy-1,3-dihydroxyacetone dimer (FIG. 7). FIG. 7 illustrates a scheme to result in a plasticizer of bis-isovalerate ester of 2,5-diisopropoxy-1,3-dihydroxyacetone dimer. The ethyl moieties can be changed to methyl, isopropyl or other organic. This structure type of plasticizer with relatively small ester moieties would be the most common type of plasticizer employed.

Figure 8:
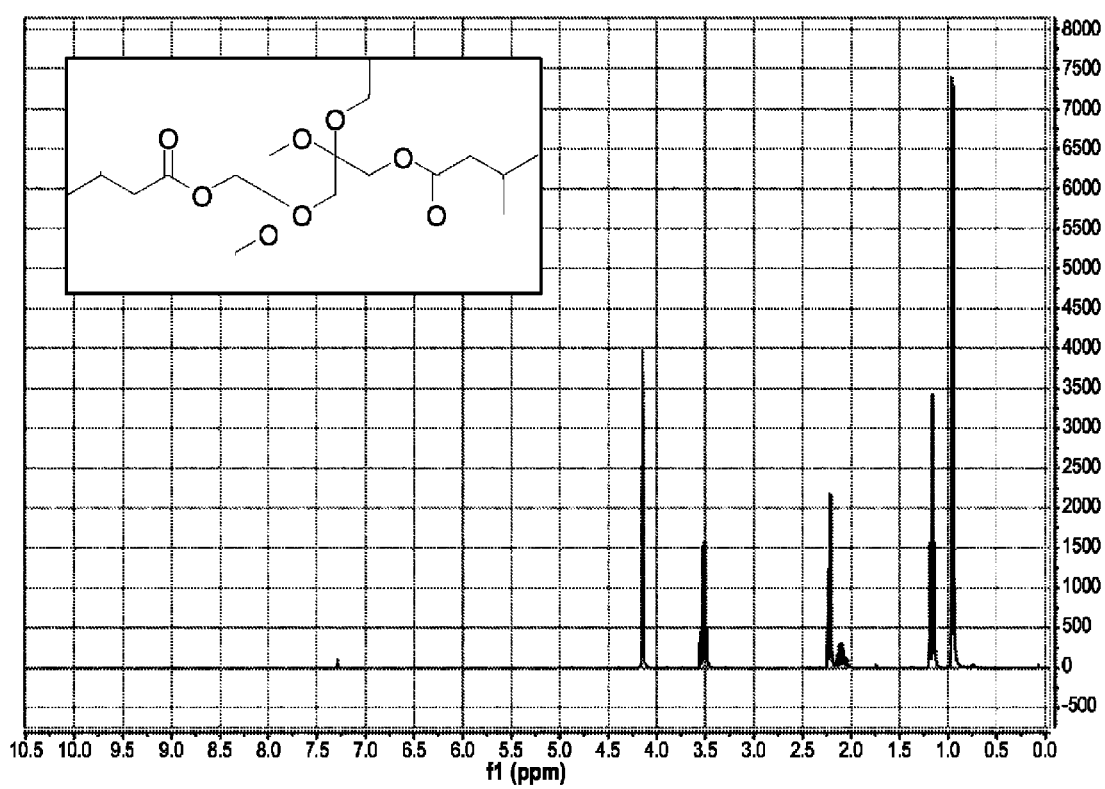
FIG. 8. $^1$H NMR of the plasticizer bis-isovalerate ester of 2,5-diethoxy-1,3-dihydroxyacetone dimer in accordance with the embodiments provided herein.

The solution was washed with dilute bicarbonate and extracted with methylene chloride and purified on silica using 2% acetone in hexanes. [1]NMR shown in FIG. 8. Overall yield is very close to quantitative.

Figure 9:
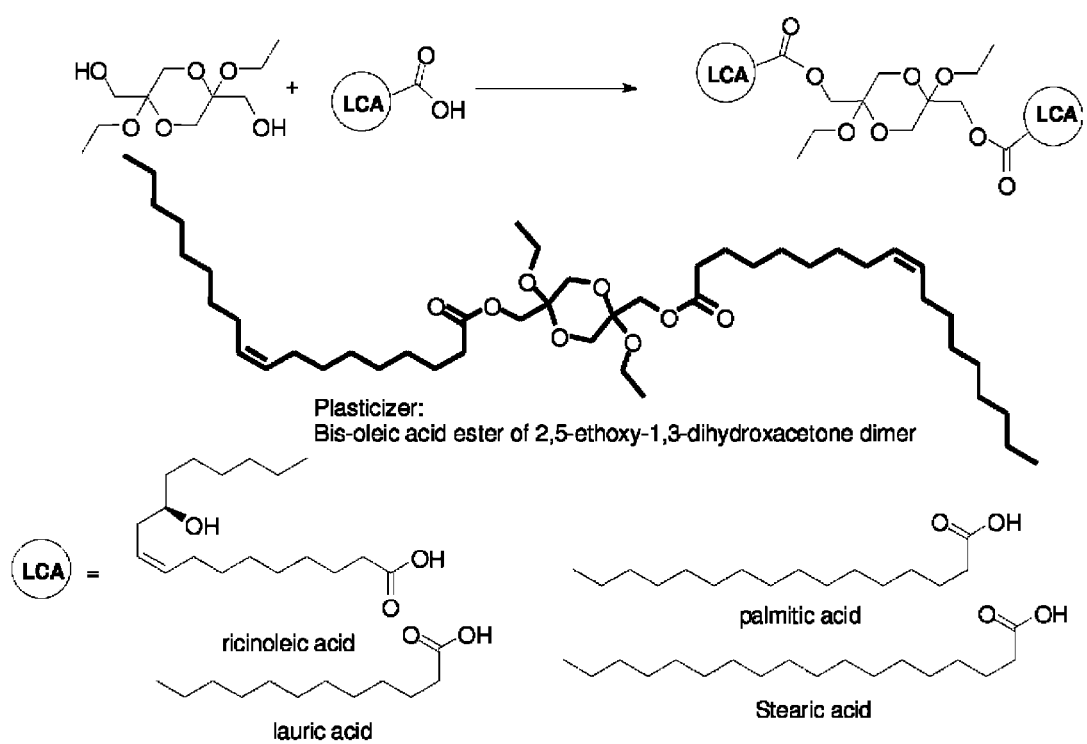
FIG. 9. Plasticizer produced from fatty acids and 2,5-diethoxy-1,3-dihydroxyacetone dimer. "LCA" stands for long chain fatty acid in accordance with the embodiments provided herein.

Plasticizers with fatty acids. Fatty acids are very large carboxylic acids derived from natural oils from plants and the seeds of plants such as linseed, cotton seed, tung, or sunflower. The fatty acids are often used in dying oils or alkyds. However, since the esters of the oils are often high boiling liquids, the fatty acids have potential as plasticizers. The common saturated fatty acids are lauric (C12), palmitic (C14), and stearic (C18), and the common unsaturated fatty acids are oleic, ricinoleic, linoleic, and linolenic (FIG. 9). Usually for plasticizers the saturated or mono-unsaturated fatty acids are used as a curing mechanism is not needed. Fatty acid type plasticizers are particularly useful for more specific applications such as those for conveyor belts, rubber balls, or for some specific olefins. Oleic acid is given as a synthesis example.

Figure 10:
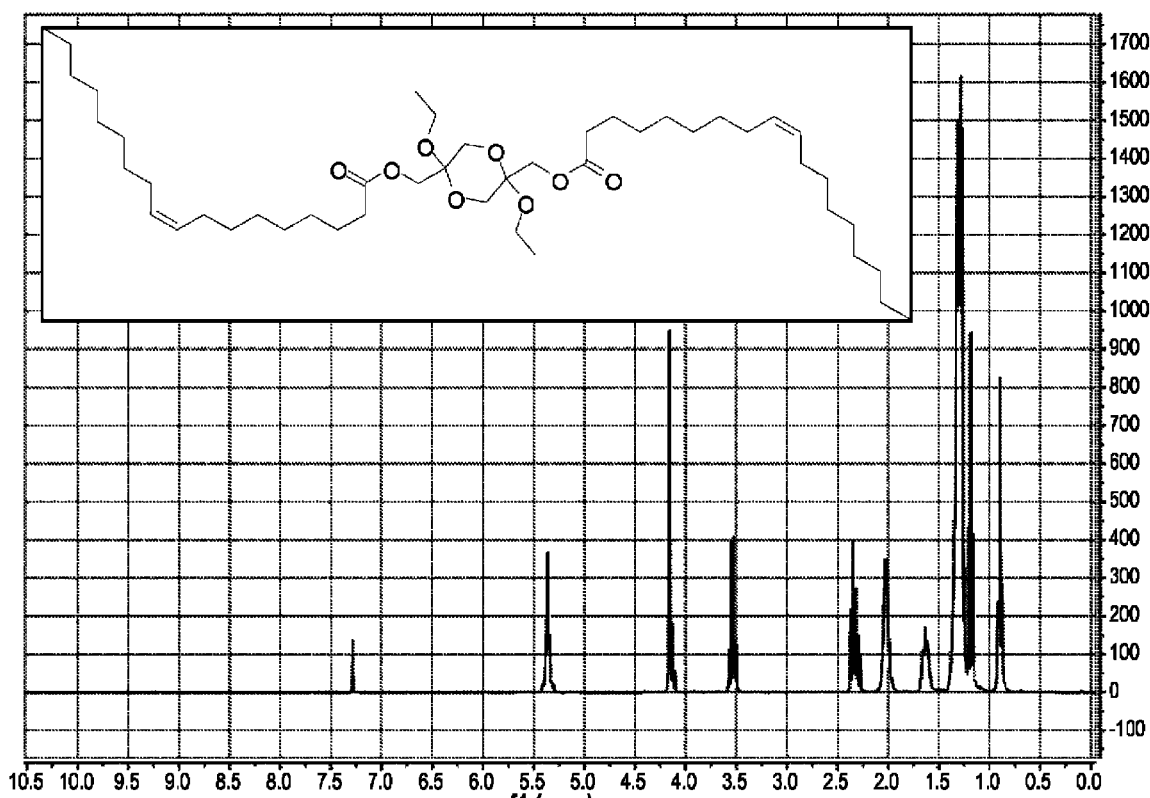
FIG. 10. $^1$H NMR in $DCCl_3$ of the plasticizer bis-oleate ester of 2,5-diethoxy-1,3-dihydroxyacetone dimer in accordance with the embodiments provided herein.

Synthesis of fatty acid-hydroxyacetone dimer plasticizers (FIG. 9). The synthesis of diolate-2,5-diethoxy-1,3-dihydroxyacetone dimer plasticizers may be accomplished through a carboxylic anhydride ester synthesis or between the direct esterification between acid and alcohol, or through the use of an acid chloride, which is described. Oleic acid chloride, 2.25 equivalents, is added dropwise to a solution of 2,5-diethoxy-1,3-dihydroxyacetone dimer (1.0 equivalents) in methylene chloride/triethylamine at 0° C. in a reaction kettle. The solution was allowed to slowly warm to room temperature overnight to form the bis-oleate ester of 2,5-diethoxy-1,3-dihydroxyacetone dimer (FIGS. 9, 10). The solution was washed with dilute bicarbonate and extracted with methylene chloride and purified on silica using 2% acetone in hexanes. [1]NMR shown in FIG. 10. Overall yield is very close to quantitative.

Referring to FIG. 9, "LCA" refers to a long-chain fatty acid. In the exemplary embodiment described herein, the LCA is oleic acid. Any LCA known to those of skill in the art is suitable for reaction according to the embodiments provided herein and FIG. 9 provides several exemplary embodiments: ricinoleic acid, lauric acid, palmitic acid, and steric acid.

The ester plasticizers are common for plastics; however, there is often a need for plasticizers that have particular properties. Concrete often requires plasticizers with greater hydrolytic stability and water solubility than what an ester plasticizer is capable of. Plasticizers used for particular coatings applications require flame retardance.

Flame resistant plasticizers. The addition of phosphorus imparts flame resistance to a material. Phosphorus may be added to hydroxyacetone or dihydroxyacetone dimers by the use of phosphinic acid and phosphoric acid. Phosphoric acid esters are very common in nature. Examples of phosphoric acid esters include DNA and RNA. Phosphinic acid are a form of organic acid that contain one phosphonyl and one hydroxyl as well as two organic side chains. Phosphinic acid produces esters that are more hydrolytically stable than those of phosphoric acid. The acute toxicity of phosphoric acid esters and phosphinic acid are very low. Bis-(2,4,4-trimethylpentyl) phosphinic acid (commonly known as Cyanex 272) has a $LD_{50}$(rat) of 3500 mg/kg and is biodegradable.[1] The degradation occurs through oxidation forming phosphoric acid and the corresponding alcohols; thus, the compound does not persist in the environment.

Figure 11:
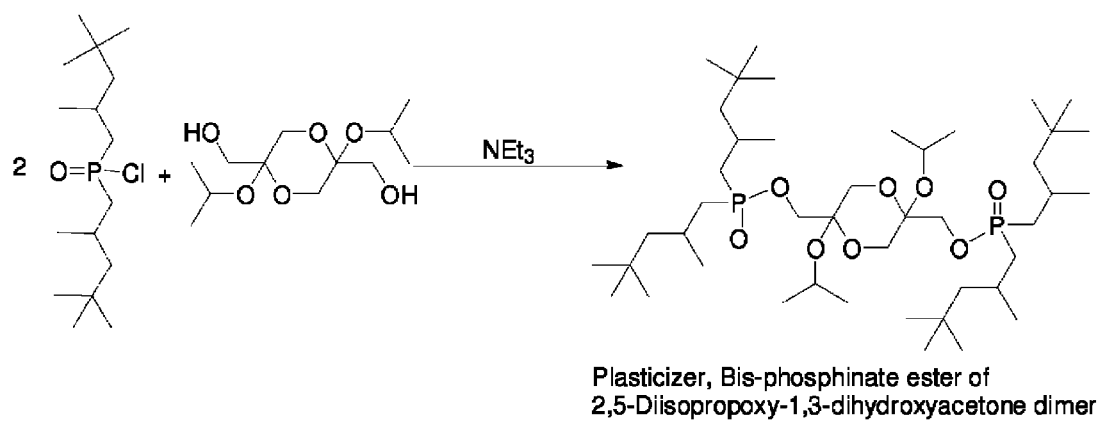
FIG. 11. Synthesis of phosphinic acid ester of 2,5-diisopropoxy-1,3-dihydroxyacetone dimer resulting in a plasticizer that is flame retardant in accordance with the embodiments provided herein.

Synthesis of phosphorus-2,5-diisopropoxy-1,3-dihydroxyacetone dimer plasticizers (FIG. 11). The synthesis of di(bis-(2,4,4-trimethylpentyl) phosphinate acetone dimer plasticizer can be accomplished through nucleophilic displacement of a chloride ester synthesis. Bis-(2,4,4-trimethylpentyl) phosphinic acid chloride (2.05 equivalents) is mixed with toluene, in a reaction kettle. The kettle is kept on an ice bath at 0° C. Triethylamine, 3 equivalents, is added to 2,5-diisopropoxy-1,3-dihydroxyacetone dimer, 1.0 equivalents, and the dimer is allowed to dissolve. The 2,5-diisopropoxy-1,3-dihydroxyacetone dimer solution is then added dropwise to bis-(2,4,4-trimethylpentyl) phosphinic acid chloride. The temperature is maintained at 0° C. Once the reaction is complete the system is placed under vacuum to remove the toluene and the resulting product washed to remove triethyl amine, triethyl amine chloride and the small amount of bis-(2,4,4-trimethylpentyl) phosphinic acid, all of which can then be recycled.

Mono-substituted derivatives of 2,5-diethoxy-1,3-dihydroxyacetone dimer. As needed to tailor the properties of a plasticizer, mono esters can be produced from 2,5-diethoxy-1,3-acetone dimer using synthetic procedures to produce bis esters of 2,5-diethoxy-1,3-acetone dimer.

Figure 12:
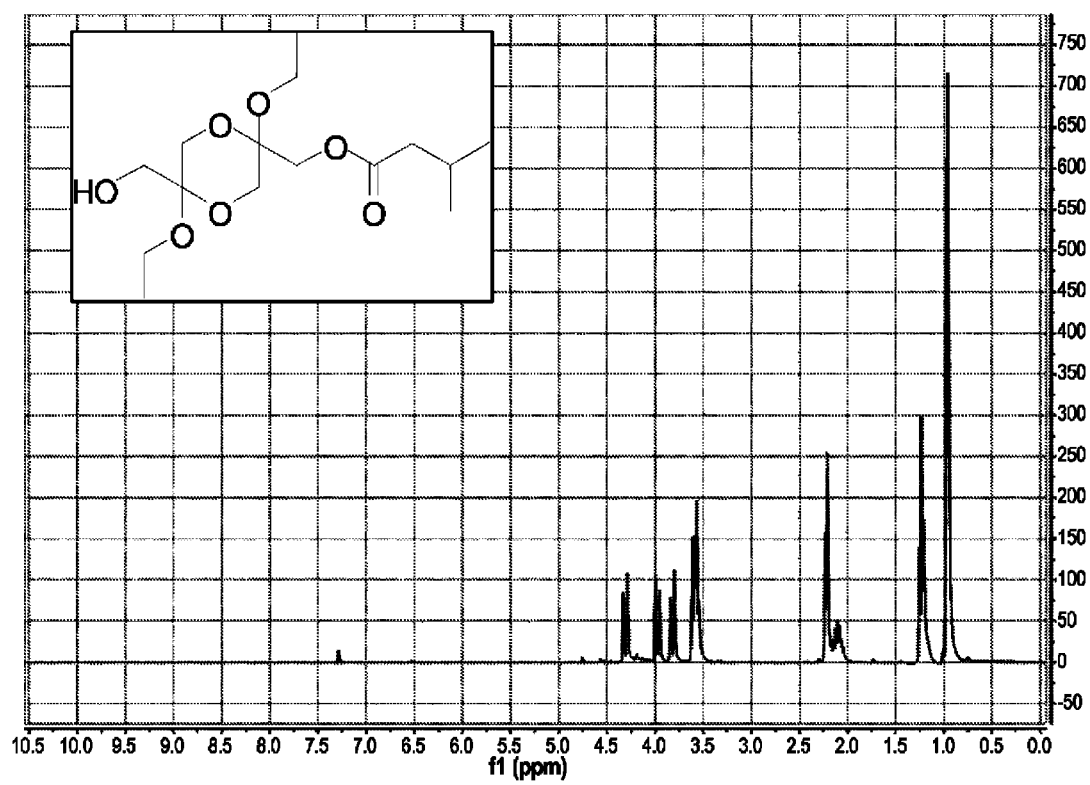
FIG. 12. $^1$H NMR in $DCCl_3$ of the plasticizer mono-isovalerate ester of 2,5-diethoxy-1,3-dihydroxyacetone dimer in accordance with the embodiments provided herein.

A $^1$H NMR of 2,5-diethoxy-1,3-acetone dimer mono-isovalerate ester is shown in FIG. 12.

Figure 13:
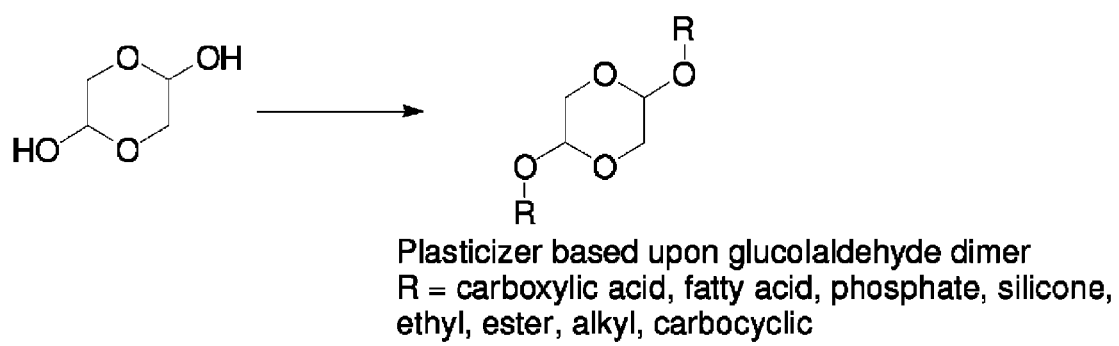
FIG. 13. Plasticizers based upon dimers of glucolaldehyde in accordance with the embodiments provided herein.

Glucose-derived plasticizers. The invention additionally includes the formation and use of dimers of glucolaldehyde (FIG. 13). Such a feedstock is desirable because it is both common and known to be benign. As the name suggests, this is a derivative of glucose. In similar chemistry presented for the acetone dimers glucolaldehyde can be made into plasticizers with carboxylic acids, fatty acids, phosphates, silicones and other moieties.

Synthesis of Dihydroxyacetone Compounds with a Chromium Trioxide Catalyst.

An exemplary synthetic route to 2,5-Diethoxy-[1,4]dioxane-2,5-dicarboxylic acid is provided.

Figure 14:
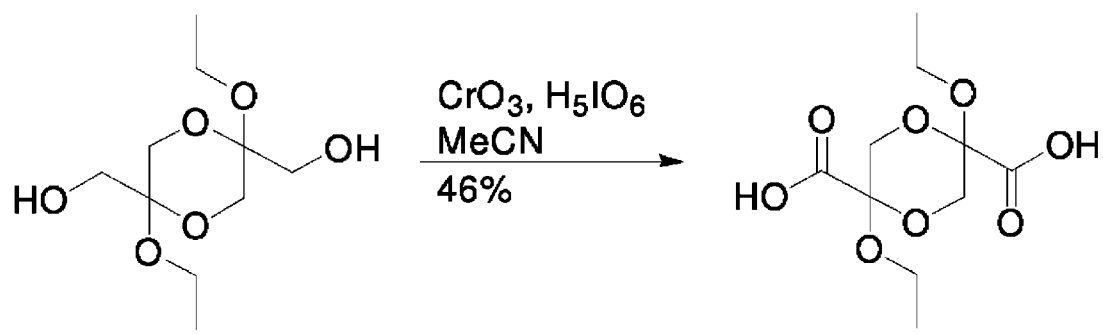
FIG. 14. Synthesis of 2,5-Diethoxy-[1,4]dioxane-2,5-dicarboxylic acid in accordance with the embodiments provided herein.

2,5-Diethoxy-[1,4]dioxane-2,5-dicarboxylic acid. A stock solution of $H_5IO_6/CrO_3$ is prepared by dissolving $H_5IO_6$ (11.4 g, 50 mmol) and $CrO_3$ (23 mg, 1.2 mol %) in MeCN (containing 0.75-1.00 v % water) to a volume of 114 mL (complete dissolution typically required 1-2 hours). The $H_5IO_6/CrO_3$ solution (92.8 mL) is then added to a solution of dihydroxyacetone dimer diethyl ether (8.0 mmol) in wet acetonitrile (40 mL, 0.75 v % water) over 45 minutes while maintaining the reaction temperature at 0-5° C. The mixture is mixed at 0° C. for 0.5 h and the completion of the reaction is confirmed by thin layer chromatography. The reaction is then quenched by adding an aqueous solution of $Na_2HPO_4$ (2.40 g in 40 mL $H_2O$). Methylene chloride (60 mL) is added and the organic layer is separated and washed with 1/1 brine/water mixture (2×40 mL) then a mixture of aqueous $NaHSO_3$ (0.88 g in 20 mL water) and finally brine (20 mL). To provide 2,5-Diethoxy-[1,4]dioxane-2,5-dicarboxylic acid, as illustrated in FIG. 14.

It will be appreciated that there are many ways to oxidize an alcohol to an acid, as accomplished in this embodiment; for example, $KMnO_4$, $RuO_4$, and Jone's Reagent through an intermediate aldehyde or oxygen can be used to form carboxylic acids from alcohols. Any such synthetic schemes are contemplated by the present invention.

Synthesis of Dihydroxyacetone Dimers Using Uronium-Based Coupling Agents.

Figure 15:
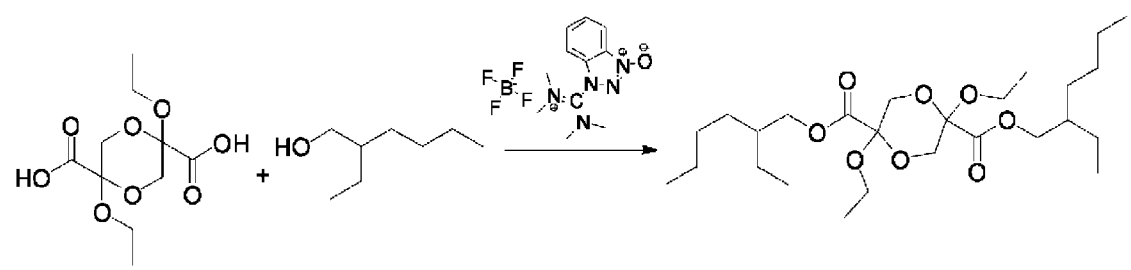
FIG. 15. Synthesis of 2,5-Diethoxy-[1,4]dioxane-2,5-dicarboxylic acid bis-(2-ethyl-hexyl) ester in accordance with the embodiments provided herein.

2,5-Diethoxy-[1,4]dioxane-2,5-dicarboxylic acid bis-(2-ethyl-hexyl) ester. In an oven-dried round-bottomed flask equipped with a magnetic stir bar, 2,5-diethoxy-[1,4]dioxane-2,5-dicarboxylic acid (2.50 mmol), 2-(1H-benzotriazole-1-yl)-1,1,3,3-tetramethyluronium tetrafluoroborate (0.80 g, 2.50 mmol), and diisopropylethylamine (0.76 mL, 5.00 mmol) are dissolved in anhydrous DMF (8 mL) and the resulting mixture was stirred at room temperature for 30 min. under an argon atmosphere. 2-ethylheanol, 1-butanol, or ethanol (5.20 mmol of hydroxyl moieties) in DMF (4 mL) is then injected into the reaction mixture via syringe and stirring is continued at room temperature until TLC confirmed the completion of the reaction (2 hours). The reaction mixture is diluted with $CH_2Cl_2$ (30 mL) and the resulting mixture was washed with 5% HCl (2×3 mL), 1M $NaHCO_3$ (3×3 mL) and water (2×3 mL). The organic layer was collected, dried ($MgSO_4$), filtered, and concentrated to give a crude ester product, which is then purified by column chromatography using ethyl acetate/acetone (98:2). To provide 2,5-Diethoxy-[1,4]dioxane-2,5-dicarboxylic acid bis-(2-ethyl-hexyl) ester, as illustrated in FIG. 15.

Hydroxyacetone plasticizers in poly(vinyl chloride) (PVC) and in poly(vinyl butyraldehyde) (PVB). In order to test the performance of hydroxyacetone-based plasticizers, exemplary plasticizers were incorporated into PVC and poly(vinyl butyraldehyde) (PVB). The resulting composites were tested for elongation and tensile strength.

Plasticizer in PVC. Poly(vinyl chlorine), MW ~93,000, was dissolved in tetrahydrofuran to create a 15.85% solids solution. 15.46 g (2.45 g solids) of the PVC solution was weighed out in a vial and 1.55 g of the plasticizer bis-isovalerate ester of 2,5-diethoxy-1,3-dihydroxyacetone dimer was added and mixed completely with the PVC solution to create a dry film 38.75% by weight plasticizer. The solution was drawn down into ribbons that had dry dimensions of 1 inch width, 12 inches in length and 0.0085 inch thickness.

15.39 g (2.44 g solids) of the PVC solution was weighed out in a vial and 0.75 g of the plasticizer bis-isovalerate ester of 2,5-diethoxy-1,3-dihydroxyacetone dimer was added and mixed completely with the PVC solution to create a dry film 23.51% by weight plasticizer. The solution was drawn down into ribbons that had dry dimensions of 1 inch width, 12 inches in length and 0.0035 inch thickness.

15.27 g (2.42 g solids) of the PVC solution was weighed out in a vial and 0.84 g of the plasticizer bis-oleate ester of 2,5-diethoxy-1,3-dihydroxyacetone dimer was added and mixed completely with the PVC solution to create a dry film 25.77% by weight plasticizer. The solution was drawn down into ribbons that had dry dimensions of 1 inch width, 12 inches in length and 0.005 inch thickness.

Plasticizer in PVB. Poly(vinyl butyraldehyde), 5.00 g MW ~100,000, was dissolved in tetrahydrofuran to create an 18.23% solids solution. 15.76 g (2.87 g solids) of the PVB solution was weighed out in a vial and 1.16 g of the plasticizer bis-isovalerate ester of 2,5-diethoxy-1,3-dihydroxyacetone dimer was added and mixed completely with the PVC solution to create a dry film 28.8% by weight plasticizer. The solution was drawn down into ribbons that had dry dimensions of 1 inch width, 12 inches in length and 0.004 inch thickness.

TABLE 2

Tensile and elongation results of 1,3-dihydroxyacetone dimers in poly(vinyl chloride) (PVC) and poly(vinyl butyraldehyde) (PVB).

| Film | Plasticizer | % Loading | Elongation (%) | Tensile (ksi) |
|---|---|---|---|---|
| PVC | None | NA | 13.15 | 1.902 |
| PVC | Bis-isovalerate | 23.51 | 44.47 | 1.213 |
| PVC | Bis-isovalerate | 38.75 | 117.59 | 0.379 |

TABLE 2-continued

Tensile and elongation results of 1,3-dihydroxyacetone dimers in poly(vinyl chloride) (PVC) and poly(vinyl butyraldehyde) (PVB).

| Film | Plasticizer | % Loading | Elongation (%) | Tensile (ksi) |
|---|---|---|---|---|
| PVC | Bis-oleate | 25.77 | 29.01 | 1.445 |
| PVB | None | N/A | 4.64 | 1.760 |
| PVB | Bis-isovalerate | 28.78 | 64.55 | 0.523 |

Figure 16:
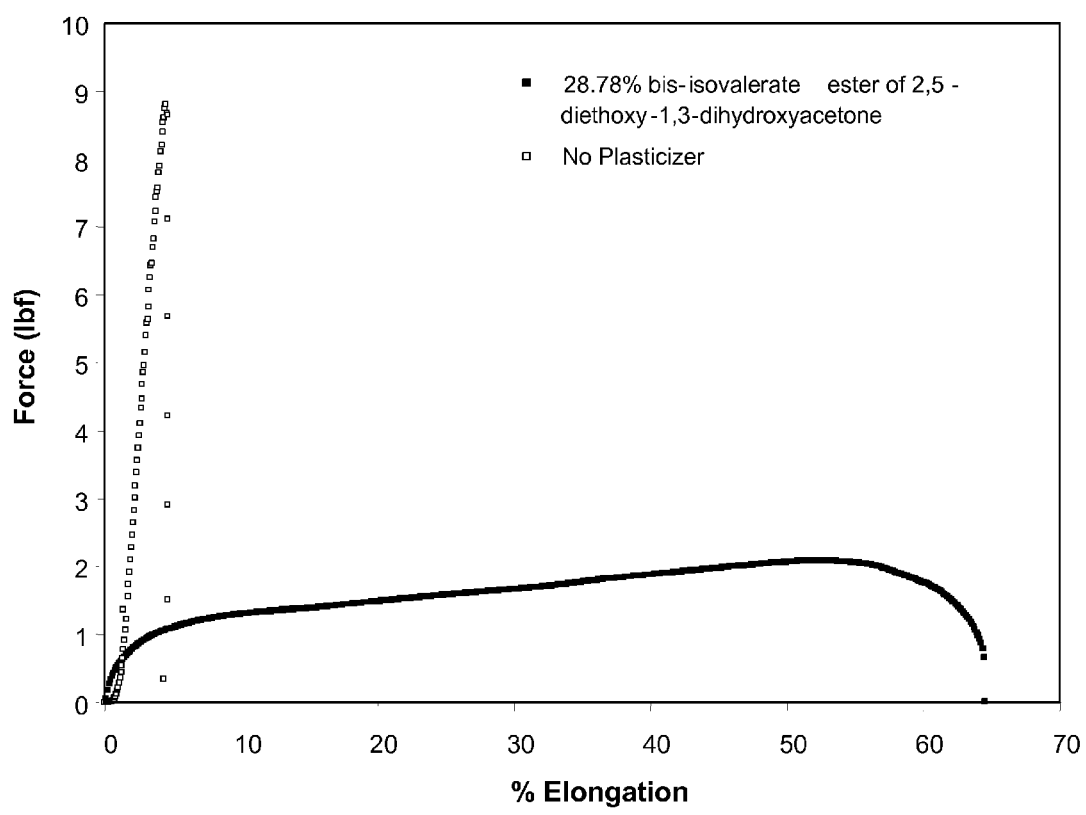
FIG. 16. Tensile and elongation of poly(vinyl butyraldehyde) neat film and with 28.78% by weight of bis-isovalerate ester of 2,5-diethoxy-1,3-dihydroxyacetone dimer in accordance with the embodiments provided herein.

The poly(vinyl chloride) and poly(vinyl butyraldehyde) ribbons were mounted between two roller-type vice grips in an Instron 5500 Tensiometer. The diameter of the roller was 1.5 inches and the ribbon was rolled around at least twice and the rollers locked to prevent slippage. The sample length once loaded in the Instron was 3 to 4 inches. The Instron was set to an extension rate of 2.0 inches per minute and the sample elongated until breakage occurred. Data from the tensile and elongation results are shown in Table 2 and FIG. 16.

According to the experimental data obtained, the plasticizers of the invention function well as plasticizers in two common polymers, PVC and PVB. Thus confirming the applicability of the provided compounds as plasticizers.

Benefits of the Compounds as Plasticizers

There are many advantages, when compared to traditional (e.g., phthalate) plasticizers, to using the acetone derivatives of the invention as the core component in plasticizers:

Cost competitive with phthalate plasticizers while being environmentally benign.

Decreased toxicity.

Does not have carcinogenic, mutagenic properties.

Does not have developmental or reproductive toxicity.

Inherently biodegradable.

Based upon acetone and carbohydrates.

Improved hydrolytic stability of plasticizers.

Greatly improved UV resistance and light stability of plasticizers allowing for outdoor usage in coatings, plastics, and in optical components.

Can be used to plasticize polyvinyl chloride.

Superplasticizers can be made for concrete.

Very high boiling point so the acetone derived plasticizer does not evaporate out of coatings and plastics.

Flame retardant plasticizers that are much more hydrophobic and do not leach into water unlike traditional phosphate esters.

Personal-Care Applications.

In addition to the described uses of the provided compounds as plasticizers, the compounds can additionally be used in personal-care application, such as perfumes and shampoos. The disclosed compounds provide a "softening" effect when incorporated into personal care products.

In this regard, below are presented an exemplary perfume and shampoo comprising compounds disclosed herein. Thus, embodiments of the invention include shampoos, hand lotion, nail polish, cologne, deodorant, hair spray, make up, lipstick, mascara, and perfumes comprising the compounds disclosed herein.

Plasticizers (perfume) will soften skin so that ethanol can be used.

Shampoo softens hair.

Figure 17:
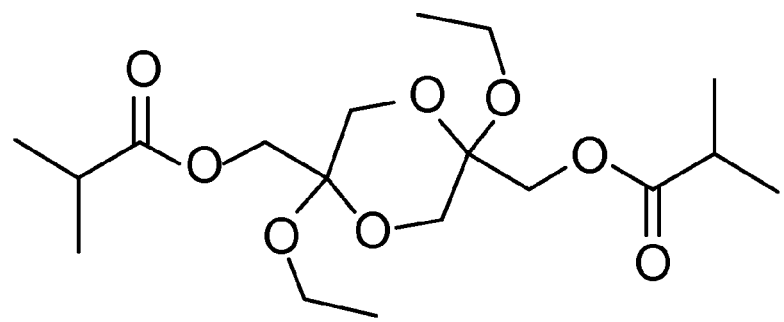
FIG. 17. Structure of isobutyric acid 2,5-diethoxy-5-isobutyryloxymethyl-[1,4]dioxan-2-ylmethyl ester, which is useful as a component in health care products in accordance with the embodiments provided herein.

Exemplary Perfume 1. Step 1. To 190 proof ethanol (Everclear) was added 1.5% by weight isobutyric acid 2,5-diethoxy-5-isobutyryloxymethyl-[1,4]dioxan-2-ylmethyl ester (the di-ethylether and di-isobutyric acid ester of 1,3-dihydroxyacetone, FIG. 17). The two were well blended together to form a solution Step 2. A fragrance blend, 50 g, was created using vanilla, sandalwood, French lavender, jasmine, ylang ylang, and dark must. Vanilla constituted 34.8% of the blend, sandalwood 26.1%, French lavender 17.4%, jasmine 8.7%, ylang ylang 8.7% and dark musk was 4.2%.

Step 3. To the blend outlined in step 1 was added 6% by weight water.

Step 4. A perfume was created using 80 g of the ethanol/dihydroxyacetone/water solution and 20 g of the fragrance blend and mixing together to form a solution.

Figure 18:
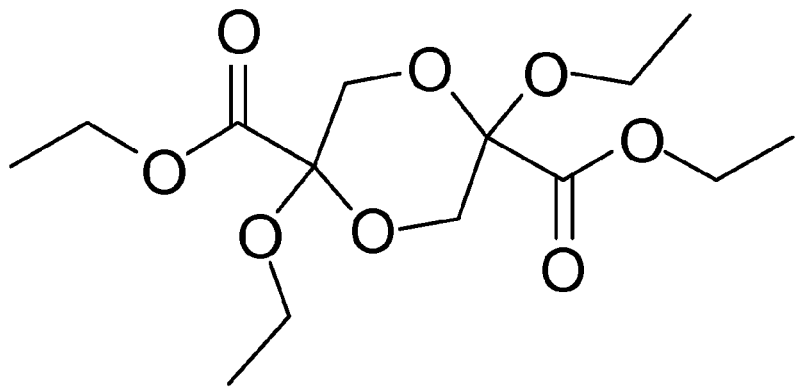
FIG. 18. Structure of 2,5-diethoxy-[1,4]dioxane-2,5-dicarboxylic acid diethyl ester, which is useful as a component in health care products in accordance with the embodiments provided herein.

Exemplary Perfume 2: Step 1. To 190 proof ethanol (Everclear) was added 1.5% by weight 2,5-diethoxy-[1,4]dioxane-2,5-dicarboxylic acid diethyl ester (FIG. 18). The two were well blended together to form a solution Step 2. A fragrance blend, 50 g, was created using vanilla, sandalwood, French lavender, jasmine, ylang ylang, and dark must. Vanilla constituted 34.8% of the blend, sandalwood 26.1%, French lavender 17.4%, jasmine 8.7%, ylang ylang 8.7% and dark musk was 4.2%.

Step 3. To the blend outlined in step 1 was added 6% by weight water.

Step 4. A perfume was created using 80 g of the ethanol/dihydroxyacetone/water solution and 20 g of the fragrance blend and mixing together to form a solution.

Figure 19:
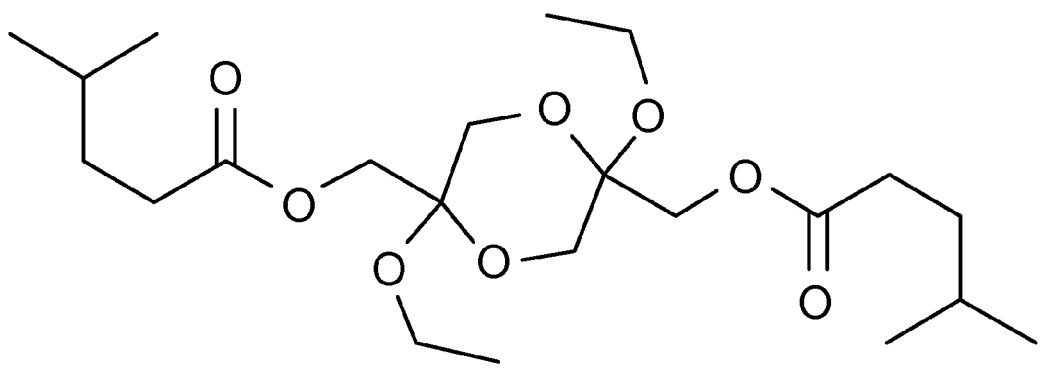
FIG. 19. Softening component used in shampoo formulation in accordance with the embodiments provided herein.

Exemplary Shampoo 1: Step 1. To a 30% by weight solution of ammonium lauryl sulfate in water (99 g) was added slowly with rapid stirring was added 0.5 g of 4-methyl-pentanoic acid 2,5-diethoxy-5-(4-methyl-pentanoyloxymethyl)-[1,4]dioxan-2-ylmethyl ester (FIG. 19).

Step 2. To a 27% by weight solution of ammonium laureth-2 sulfate in water (99 g) was added 0.3 g of 4-methyl-pentanoic acid 2,5-diethoxy-5-(4-methyl-pentanoyloxymethyl)-[1,4]dioxan-2-ylmethyl ester.

Step 3. To 26.0 g of the ammonium laureth-2 sulfate mixture was added 10.0 g of the ammonium lauryl sulfate mixture to create the starting surfactant mixture (SSM).

Step 4. To the SSM was added 2.0 g of cocamide diethanolamine.

Step 5. Then 6.0 g cocamidopropyl betaine was added to the SSM.

Step 6. The pH was adjusted to 5.7-6.1 using citric acid.

Step 7. 0.5 g of vanilla extract was added to add a pleasing odor.

Step 8. The shampoo was created by diluting the combined mixture of steps 1-7 with roughly 55 g of water to give roughly 100 g of shampoo.

Exemplary Shampoo 2. Step 1. To a 30% by weight solution of ammonium lauryl sulfate in water (99 g) was added slowly with rapid stirring was added 0.5 g of 2,5-diethoxy-[1,4]dioxane-2,5-dicarboxylic acid diethyl ester (FIG. 18).

Step 2. To a 27% by weight solution of ammonium laureth-2 sulfate in water (99 g) was added 0.3 g of 2,5-diethoxy-[1,4]dioxane-2,5-dicarboxylic acid diethyl ester.

Step 3. To 26.0 g of the ammonium laureth-2 sulfate mixture was added 10.0 g of the ammonium lauryl sulfate mixture to create the starting surfactant mixture (SSM).

Step 4. To the SSM was added 2.0 g of cocamide diethanolamine.

Step 5. Then 6.0 g cocamidopropyl betaine was added to the SSM.

Step 6. The pH was adjusted to 5.7-6.1 using citric acid.

Step 7. 0.5 g of vanilla extract was added to add a pleasing odor.

Step 8. The shampoo was created by diluting the combined mixture of steps 1-7 with roughly 55 g of water to give roughly 100 g of shampoo.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A plasticizer, comprising a compound:

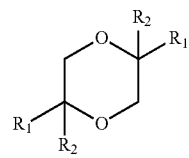

wherein $R_1$ is independently selected from —O—$R_3$ and —$CH_2$—O—$R_3$;

wherein $R_2$ is independently selected from H, —O—$R_3$, C—O—C(O)—$R_3$, C—O—X(O)$_{1\,or\,2\,or\,3}$—$R_3$ where X is C, Si, Ge, Sn, Pb, P, As, Sb, Bi, S, Se, Te; methyl, lower alkane, ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety; and wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

2. The plasticizer of claim 1, wherein the compound is formed by the reaction of a hydroxyacetone dimer and a carboxylic acid or a reaction between carboxylic acid derived from 1-hydroxyacetone dimer and a 1,3-dihydroxyacetone dimer and an alcohol.

3. The plasticizer of claim 1, wherein $R_3$ is a naturally occurring acid or alcohol.

4. The plasticizer of claim 3, wherein the naturally occurring acid or alcohol is selected and derived from the group consisting of animal fatty acids and/or alcohols, animal acids and/or alcohols, vegetation fatty acids and/or alcohols, vegetation acids and/or alcohols, bacteria derived acids and/or alcohols, single cell organism derived acids and/or alcohols, virus derived acids and/or alcohols, and fruit-derived acids and/or alcohols.

5. The plasticizer of claim 1, wherein the plasticizer or compound is selected from the group consisting of biodegradable, biocompatible, low in toxicity, non-carcinogenic, not harmful to the reproductive tract, non-mutagenic, non-teratogenic, and low in health consequences.

6. The plasticizer of claim 1, wherein the plasticizer has a boiling point of 100° C. or greater.

7. The plasticizer of claim 1, wherein the plasticizer has a freezing point of 20° C. or less.

8. The plasticizer of claim 1, wherein the plasticizer is a liquid.

9. The plasticizer of claim 1, wherein the plasticizer is a solid.

10. The plasticizer of claim 1, wherein the plasticizer is colorless.

11. The plasticizer of claim 1, wherein the plasticizer is tasteless.

12. The plasticizer of claim 1, wherein the plasticizer has taste.

13. The plasticizer of claim 1, wherein the plasticizer is incorporated into a polymer matrix.

14. The plasticizer of claim 1, wherein the plasticizer is a dimer of a glucolaldehyde, or a derivative thereof.

15. A composite, comprising:
(a) concrete; and
(b) a plasticizer of claim 1 incorporated into the concrete.

16. A composite, comprising:
(a) a polymer; and
(b) a plasticizer of claim 1 incorporated into the polymer.

17. A health care product, comprising a plasticizer of claim 1 incorporated into a product selected from the group consisting of a perfume, a cologne, a hand lotion, a nail polish, a hair spray, a deodorant, a sanitizer, a soap, a mascara, a lipstick, an eye liner, a blush, an anti-acne composition, and makeup.

18. A compound:

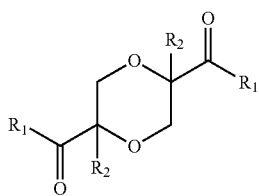

wherein $R_1$ and $R_2$ are independently selected from the group consisting of:

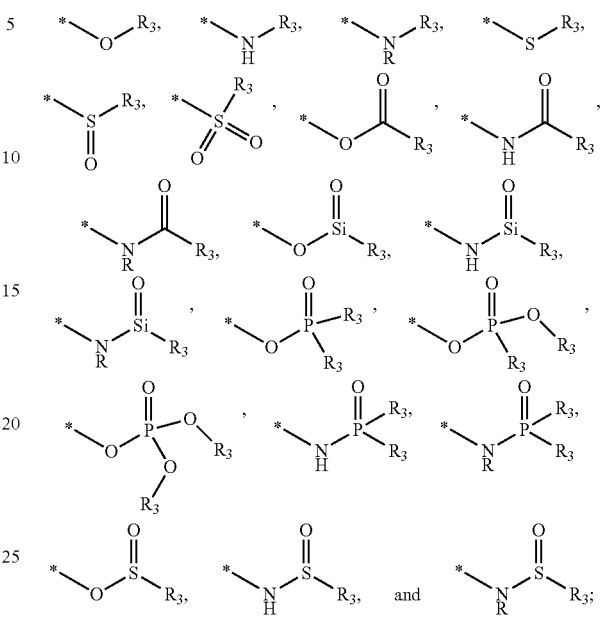

wherein $R_3$ is independently selected from ether, ester, alkyl, aromatic, silicon-containing moiety, phosphorous containing moiety, sulfur containing moiety, cycloaliphatic, urethane, fatty acid, fluorinated alkyl moiety, chlorinated alkyl moiety, brominated alkyl moiety, nitrogen containing alkyl moiety, nitrogen containing aromatic moiety, oxygen containing alkyl moiety, phosphorous containing alkyl moiety, sulfur containing alkene moiety, tin containing alkyl moiety, lead containing alkyl moiety, boron containing alkyl moiety, alkyne moiety, fluorine containing moiety, chlorine containing moiety, bromine containing moiety, iodine containing moiety, oxygen containing moiety, sulfur containing moiety, selenium containing moiety, tellurium containing moiety, nitrogen containing moiety, phosphorus containing moiety, arsenic containing moiety, antimony containing moiety, bismuth containing moiety, carbon containing moiety, silicon containing moiety, germanium containing moiety, tin containing moiety, lead containing moiety, boron containing moiety, aluminum containing moiety, metal containing moiety, and a transition metal containing moiety.

19. A plasticizer, comprising a compound selected from the group consisting of a 1-hydroxyacetone dimer, a 1,3-dihydroxyacetone dimer, 2,5-dihydroxy-[1,4]dioxane-2,5-dicarboxylic acid, 2,5-bis-hydroxymethyl-[1,4]dioxane-2,5-diol, (5-hydroxymethyl-2,5-dimethyl-[1,4]dioxan-2-yl)-methanol, 2,5-Dimethyl-[1,4]dioxane-2,5-dicarboxylic acid, a carboxylic acid derived from 1-hydroxyacetone dimer, and a carboxylic acid derived from a 1,3-dihydroxyacetone dimer.

* * * * *